United States Patent [19]
Arimura et al.

[11] 4,450,275
[45] May 22, 1984

[54] CYCLIC IMINOCARBOXYLIC ACID DERIVATIVES

[75] Inventors: Katsuo Arimura, Oita; Shu Murakami, Fukuoka; Taichi Oka, Oita, all of Japan

[73] Assignee: Yoshitomi Pharmaceutical Industries, Ltd., Osaka, Japan

[21] Appl. No.: 227,104
[22] PCT Filed: Sep. 28, 1980
[86] PCT No.: PCT/JP79/00249
§ 371 Date: Jun. 5, 1980
§ 102(e) Date: Jun. 5, 1980
[87] PCT Pub. No.: WO80/00700
PCT Pub. Date: Apr. 17, 1980

[30] Foreign Application Priority Data
Oct. 5, 1978 [JP] Japan .................. 53-123189

[51] Int. Cl.³ .................. C07D 207/16; C07D 277/04
[52] U.S. Cl. .................. 548/201; 548/533; 424/270; 424/274
[58] Field of Search .................. 548/200, 201, 533

[56] References Cited
U.S. PATENT DOCUMENTS
4,105,776 8/1978 Ondetti et al. .................. 424/274
4,108,886 8/1978 Ondetti et al. .................. 260/455 R
4,192,878 3/1980 Ondetti .................. 548/201
4,282,235 8/1981 Ondetti .................. 548/201

FOREIGN PATENT DOCUMENTS
2006759 5/1979 United Kingdom .
2010675 7/1979 United Kingdom .

Primary Examiner—Richard Raymond
Attorney, Agent, or Firm—Sughrue, Mion, Zinn, Macpeak & Seas

[57] ABSTRACT

A cyclic iminocarboxylic acid derivative of the formula:

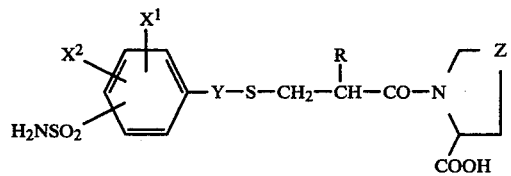

or a salt thereof, wherein $X^1$ and $X^2$ are each hydrogen, halogen, lower alkoxy, lower alkyl, trifluoromethyl, nitro, amino, alkylamino, aralkylamino, acetylamino or ethoxycarbonylamino, Y is —CO— or —SO$_2$—, Z is —CH$_2$— or —S—, and R is hydrogen or lower alkyl. Such compounds are useful as antihypertensive agents.

3 Claims, No Drawings

CYCLIC IMINOCARBOXYLIC ACID DERIVATIVES

FIELD OF THE INVENTION

This invention relates to cyclic iminocarboxylic acid derivatives which are therapeutically useful as antihypertensive agents.

DESCRIPTION OF THE INVENTION

According to the present invention, there is provided a cyclic iminocarboxylic acid derivative of the formula:

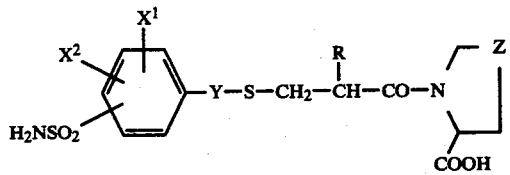

wherein $X^1$ and $X^2$ are each hydrogen, halogen (F, Cl or Br), lower alkoxy (e.g. methoxy or ethoxy), lower alkyl (e.g. methyl or ethyl), trifluoromethyl, nitro, amino, alkylamino (e.g. methylamino, dimethylamino or ethylamino), aralkylamino (e.g. benzylamino, phenethylamino or furfurylamino), acetylamino or ethoxycarbonylamino, Y is —CO— or —$SO_2$—, Z is —$CH_2$— or —S—, and R is hydrogen or lower alkyl (e.g. methyl, ethyl, propyl, isopropyl, butyl or isobutyl).

The compounds of formula (I) can be produced by one of the following Methods I ot IV.

Method I

A method of reacting a compound of the formula:

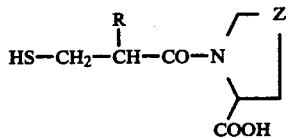 (II)

wherein R and Z are as defined above, with a functional derivative of an acid of the formula:

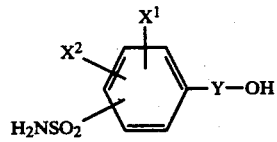 (III)

wherein $X^1$, $X^2$ and Y are as defined above.

The functional derivative of an acid of formula (III) includes an acid halide (e.g. acid chloride or acid bromide), an reactive ester (e.g. methanesulfonic acid ester or toluenesulfonic acid ester) and the like.

The reaction is usually carried out in a solvent such as water, dimethylformamide, dioxane, methylene chloride or chloroform, in the presence of an acid acceptor such as sodium hydrogen carbonate, sodium carbonate, potassium carbonate, sodium hydroxide, potassium hydroxide, triethylamine or pyridine, at room temperature or if necessary under heating or under cooling.

Method II

A method of reacting a compound of the formula:

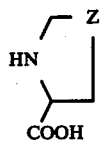 (IV)

wherein Z is as defined above, with a carboxylic acid of the formula:

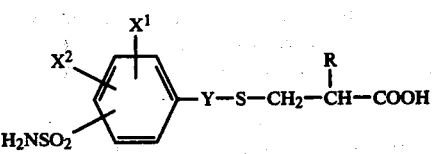 (V)

or a functional derivative thereof, wherein $X^1$, $X^2$, Y and R are as defined above.

The functional derivative of a carboxylic acid of formula (V) includes an acid chloride, an acid bromide, an acid anhydride, a mixed acid anhydride which is formed by a conventional reaction of a carboxylic acid of formula (V) with an alkyl halocarbonate (e.g. ethyl chlorocarbonate or isobutyl chlorocarbonate), a sulfonyl halide (e.g. mesyl chloride or tosyl chloride) or an inorganic acid halide (e.g. thionyl chloride, phosphorus oxychloride or phosphorus trichloride), a reactive ester (e.g. p-nitrophenyl ester or polychlorophenyl ester) and the like.

The reaction is usually carried out in a solvent such as methylene chloride, chloroform, ether, benzene, toluene, dioxane, dimethylformamide or water, if necessary in the presence of an acid acceptor such as triethylamine, dimethylaniline, pyridine, sodium hydrogen carbonate, potassium hydrogen carbonate, sodium carbonate, potassium carbonate, sodium hydroxide or potassium hydroxide, at room temperature, if necessary under heating or under cooling.

Method III

A method of reating a compound of the formula:

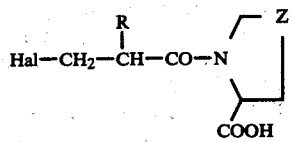 (VI)

wherein R and Z are as defined above, and Hal is halogen (e.g. Cl or Br), with a compound of the formula:

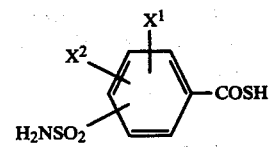 (VII)

or a metal salt thereof (e.g. sodium salt or potassium salt), wherein $X^1$ and $X^2$ are as defined above.

The reaction is usually carried out under the conditions mentioned in Method I.

Method IV

A method of reacting a compound of the formula:

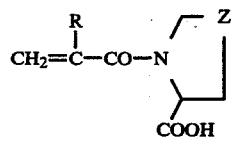 (VIII)

wherein R and Z are as defined above, with a compound of formula (VII) mentioned above.

The reaction is usually carried out in a solvent such as ethanol, methylene chloride, dioxane, dimethylformamide, benzene or toluene, at room temperature.

The cyclic iminocarboxylic acid derivatives of formula (I) are present as stereoisomers or as mixtures of these isomers. All of these are within the scope of the present invention. A mixture of the isomers, if desired, may be separated into the individual isomers in a conventional manner such as fractional crystallization or chromatography. When a starting compound is used in an optically active form, compounds of formula (I) can be produced stereo-selectively.

Preferred configurations of compounds of the present invention are those wherein:

(1) the carbon bearing the carboxyl group in the thiazolidine ring (i.e., the case where X is —S—) is R-configuration, (2) the carbon bearing the carboxyl group in the pyrrolidine ring (i.e., the case where X is —CH$_2$—) is S-configuration, and (3) when R is lower alkyl, the α-carbon in the acyl side chain is S-configuration.

The compounds of formula (I) can be converted in a conventional manner into the metal salts such as sodium salt and potassium salt, the organic base salts such as dicyclohexylamine salt, diethanolamine salt, piperazine salt, N-methylpiperazine salt, N-methyl-D-glucamine salt and trimethylolaminomethane salt, and the amino acid salts such as glycine salt, lysine salt and arginine salt.

The present invention has been accomplished on the basis of the fact that the cyclic iminocarboxylic acid derivatives of formula (I) have diuretic activities in mice and rats and potent hypotensive activities in spontaneously hypertensive rats and renal hypertensive rats, and therefore they are useful as antihypertensive agents for the treatment of essential hypertension, renal hypertension and malignant hypertension.

The compounds of formula (I) can be used in the form of a pharmaceutical preparation with a suitable and conventional pharmaceutically acceptable carrier. The pharmaceutical preparations can take any conventional form such as tablets, capsules, granules, powder or injectable solutions.

The following is an example of formulations when a compound of the invention is administered for pharmaceutical purposes: Tablets (50 mg and the 100 mg) are prepared from the following compositions:

|  | 50 mg Tablet | 100 mg Tablet |
|---|---|---|
| Compound I | 50 mg | 100 mg |
| Cornstarch | 20 mg | 20 mg |
| Lactose | a proper quantity | a proper quantity |
| Microcrystalline cellulose | 10 mg | 20 mg |
| Talc | 6 mg | 6 mg |
| Magnesium stearate | 0.5 mg | 0.6 mg |
| Methyl cellulose | 1 mg | 1.3 mg |

The daily dose of compound (I) for human adults usually ranges from about 10 mg to about 1500 mg for oral administration, in single or multiple dose, but it may vary depending upon the age, body weight, and/or severity of the conditions to be treated as well as the response to the medication.

The present invention will be better understood from the following examples, but they are not to be construed as limiting the present invention.

EXAMPLE 1

2.5 g of 3-[3-mercapto-2(S)-methylpropionyl]-4(R)-thiazolidinecarboxylic acid and 2 g of sodium hydrogen carbonate are added to 150 ml of water whereupon 2.5 g of 4-chloro-3-sulfamoylbenzoyl chloride is added slowly under ice-cooling and stirring, and the resulting mixture is stirred at room temperature for 3 hours. The reaction mixture is then made acidic with dilute hydrochloric acid under ice-cooling, and the non-crystalline solid is extracted with ethyl acetate. The extract is washed with water, dried over anhydrous magnesium sulfate, and concentrated under reduced pressure. The non-crystalline solid thus obtained is purified by column chromatography on silica gel with ethyl acetate-hexane (4:1) eluants. Thus is obtained 3-[3-(4-chloro-3-sulfamoylbenzoylthio)-2(S)-methylpropionyl]-4(R)-thiazolidinecarboxylic acid as white non-crystalline powder, $[\alpha]_D^{25} - 118.8$ (methanol). The dicylohexylamine salt of this product has a melting of 173°–176° C.

EXAMPLE 2

3 g of L-proline and 2 g of sodium hydrogen carbonate are added to 120 ml of water whereupon 3.5 g of 3-(4-chloro-3-sulfamoylbenzoylthio)-2(S)-methylpropionyl chloride is added slowly under ice-cooling and stirring, and the resulting mixture is stirred at room temperature for 3 hours. The reaction mixture is then treated in an analogous manner of Example 1 to give 1-[3-(4-chloro-3-sulfamoylbenzoylthio)-2(S)-methylpropionyl]-L-proline as white non-crystalline powder, $[\alpha]_D^{25} - 102.3$ (methanol).

EXAMPLE 3

7.0 g of 3-(2-methoxy-5-sulfamoylbenzoylthio)-2(S)-methylpropionyl chloride is reacted with 2.4 g of L-proline in water in the presence of sodium carbonate in an analogous manner of Example 2 to give 1-[3-(2-methoxy-5-sulfamoylbenzoylthio)-2(S)-methylpropionyl]-L-proline.

EXAMPLE 4

A solution of 4.2 g of 3-(4-chloro-3-sulfamoylbenzoylthio)-2-methylpropionyl chloride in 15 ml of ether is added dropwise to a mixture of 1.6 g of L-proline, aqueous 1 N potassium carbonate solution and 20 ml of ether under ice-cooling and stirring, and the resulting mixture is stirred at room temperature for 2 hours. The aqueous layer is then collected and acidic with dilute hydrochloric acid, and the separated oil is extracted with ethyl acetate. The extract is washed with water, dried over anhydrous magnesium sulfate, and concentrated under reduced pressure. The residue is dissolved in acetonitrile and 2 g of dicylohexylamine is added. The oil thus obtained is washed several times with acetonitrile by decantation. The resulting crystals are recrystallized from isopropanol to give dicylohexylamine salt of 1-[3-(4-chloro-3-sulfamoylbenzoylthio)-2(S)-methylpropionyl]-L-proline as white crystalline powder, melting at 143°–146° C.

EXAMPLE 5

A solution of 1.4 g of potassium carbonate in 30 ml of water is added to 2.8 g of 3-(3-bromo-2-methylpropionyl)-4(R)-thiazolidinecarboxylic acid whereupon 3 g of potassium 4-chloro-3-sulfamoyl-thiobenzoate is added slowly under ice-cooling and stirring, and the resulting mixture is stirred at room temperature for 4 hours. The reaction mixture is then treated in an analogous manner of Example 1, and the oily residue thus obtained is converted in a conventional manner into the dicyclohexylamine salt. Thus is obtained dicyclohexylamine salt of 3-[3-(4-chloro-3-sulfamoylbenzoylthio)-2(S)-methylpropionyl]-4(R)-thiazolidinecarboxylic acid as white crystalline powder, melting at 173°–176° C. (recrystallized twice from isopropanol).

EXAMPLE 6

5 g of 4-chloro-3-sulfamoyl-thiobenzoic acid is added slowly to a stirred solution of 3.6 g of 1-(2-methyl-2-propenoyl)-L-proline in 50 ml of ethanol at room temperature. The resulting mixture is stirred overnight and then concentrated under reduced pressure. To the residue are added ethyl acetate and water. The organic layer is washed with water, dried over anhydrous magnesium sulfate and concentrated under reduced pressure. The residue is treated in an analogous manner of Example 4 to give dicyclohexylamine salt of 1-[3-(4-chloro-3-sulfamoylbenzoylthio)-2(S)-methylpropionyl]-L-proline as white crystalline powder, melting at 143°–146° C.

The following cyclic iminocarboxylic acid derivatives of formula (I) are produced in an analogous manner of Examples 1 to 6:

1-[3-(4-chloro-3-sulfamoylbenzoylthio)propionyl]-L-proline, $[\alpha]_D^{25} = -39.9$ (1% methanol); the dicyclohexylamine salt, m.p. 205°–208° C. (decomposition)

3-[3-(4-chloro-3-sulfamoylbenzoylthio)propionyl]-4(R)-thiazolidinecarboxylic acid 1-[3-(4-chloro-2-furfurylamino-5-sulfamoylbenzoylthio)-2(S)-methylpropionyl]-L-proline 1-[3-(4-chloro-3-sulfamoylphenylsulfonylthio)-2-(S)-methylpropionyl]-L-proline 1-[3-(2-amino-4-chloro-5-sulfamoylbenzoylthio)-2(S)-methylpropionyl]-L-proline 1-[3-(3-sulfamoyl-4-trifluoromethylbenzoylthio)-2(S)-methylpropionyl]-L-proline Preparation of Starting Materials of Formula (V)

3 g of 2(S)-methyl-3-mercaptopropionic acid is added to a mixture of 3.5 g of potassium carbonate, 60 ml of water and 30 ml of ether with stirring at room temperature under a nitrogen atmosphere whereupon 6.3 g of 4-chloro-3-sulfamoylbenzoyl chloride is added, and the resulting mixture is stirred at room temperature for 5.5 hours. The aqueous layer is then collected and made acidic with dilute hydrochloric acid, and the separated oil is extracted with ethyl acetate. The extract is washed with water, dried over anhydrous magnesium sulfate, and concentrated under reduced pressure. Isopropyl ether is added to the residual oil. The crystals thus obtained are recrystallized from a mixture of ethyl acetate and hexane to give 3-(4-chloro-3-sulfamoylbenzoylthio)-2(S)-methylpropionic acid as white crystalline powder, melting at 152°–153° C. (sintering at 145° C.).

The following starting materials of formula (V) are prepared in an analogous manner:

3-(4-chloro-3-sulfamoylbenzoylthio)-2-methylpropionic acid, melting at 155°–159° C. (this product is also prepared by reacting methacrylic acid with 4-chloro-3-sulfamoyl-thiobenzoic acid (mp. 170°–174° C.)); and 3-(4-chloro-3-sulfamoylbenzoylthio)propionic acid, melting at 167°–170° C.

Although the present invention has been adequately discussed in the foregoing specification and examples included therein, one readily recognizes that various changes and modifications may be made without departing from the spirit and scope thereof.

What is claimed is:

1. A cyclic iminocarboxylic acid of the formula

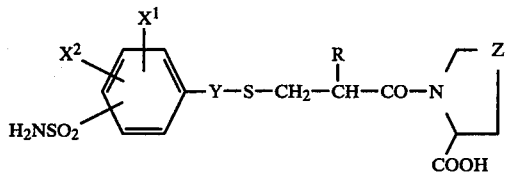

or a salt thereof, wherein $X^1$ is chlorine at the 4-position, $X^2$ is hydrogen, the $H_2NSO_2$-group is at the 3-position, Y is —CO—, Z is —CH$_2$— or —S—, and R is hydrogen or lower alkyl.

2. The compound of claim 1:
3-[3-(4-chloro-3-sulfamoylbenzoylthio)-2-(S)-methylpropionyl]-4(R)-thiazolidinecarboxylic acid.

3. The compound of claim 1:
1-[3-(4-chloro-3-sulfamoylbenzoylthio)-2-(S)-methylpropionyl]-L-proline.

* * * * *